US00PP09358P

United States Patent [19]

Bradford et al.

[11] Patent Number: Plant 9,358

[45] Date of Patent: Nov. 7, 1995

[54] NECTARINE TREE 'FIRE PEARL'

[76] Inventors: Lowell G. Bradford, 12439 E. Savana Rd.; Norman G. Bradford, 11875 E. Savana Rd., both of, Le Grand, Calif. 95333

[21] Appl. No.: 383,901

[22] Filed: Feb. 6, 1995

[51] Int. Cl.[6] ..... A01H 5/00

[52] U.S. Cl. ..... Plt./40.1

[58] Field of Search ..... Plt./40.1

[56] References Cited

U.S. PATENT DOCUMENTS

P.P. 6,363 11/1988 Bradford et al. ..... Plt./41
P.P. 7,193 3/1990 Bradford et al. ..... Plt./41
P.P. 8,461 11/1993 Bradford et al. ..... Plt./40.1

*Primary Examiner*—James R. Feyrer

[57] ABSTRACT

The present invention relates to a nectarine tree and more particularly to a new and distinct variety broadly characterized by a large size, vigorous, productive and regular bearing tree. The fruit matures under the ecological conditions described approximately the last week in July, with first picking on Jul. 29, 1994. The fruit is uniformly large in size, non-acidic in flavor, globose in shape, clingstone in type, very firm in texture, and nearly full red in skin color. The variety was a first generation cross using Red Glen (U.S. Plant Pat. No. 7,193) yellow flesh nectarine as the selected seed parent an unnamed white flesh nectarine seedling as the selected pollen parent, which was previously developed by crossing August Red (U.S. Plant Pat. No. 6,363) nectarine by Bradcrim (U.S. Plant Pat. No. 8,461) nectarine.

1 Drawing Sheet

BACKGROUND OF THE VARIETY

In a continuing effort to improve the quality of fresh market and shipping fruits, we, the inventors, typically hybridize a large number of nectarine and peach seedlings each year. The present invention relates to a new and distinct variety of nectarine tree, which has been denominated varietally as "Fire Pearl". The present variety was developed by us in 1991 in a cultivated area of our experimental orchard at Bradford Farms near Le Grand, Calif. in Merced County (San Joaquin Valley). It was a first generation cross using Red Glen (U.S. Plant Pat. No. 7,193) yellow flesh nectarine as the seed parent and an unnamed white flesh nectarine seedling as the selected pollen parent. This unnamed pollen parent was previously developed by crossing August Red (U.S. Plant Pat. No. 6,363) nectarine by Bradcrim (U.S. Plant Pat. No. 8,461) nectarine. Subsequent to origination of the present variety of nectarine tree, we asexually reproduced it by budding and grafting, and such reproduction of plant and fruit characteristics were true to the original plant in all respects.

The fruit produced by the present variety is most similar to its pollen grandparent, the Bradcrim (U.S. Plant Pat. No. 8,461), by producing white flesh nectarines that are non-acidic in flavor and virtually free from red texture bleeding, but is distinguished therefrom and an improvement thereon by producing fruit that ripens thirty days later, that is much firmer in texture, that is much sweeter in flavor, and that is clingstone instead of freestone.

The present variety is similar to both its seed parent, Red Glen (U.S. Pat. No. 7,193) and its pollen grandparent, August Red (U.S. Plant Pat. No. 6,363), by producing nectarines that are large sized, clingstone, very firm, and nearly full red in skin color, but is very distinguished from both by producing fruit that is white flesh instead of yellow flesh, and that is non-acidic in flavor instead of acidic.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of hard ripe on Aug. 1, 1994. All major color code designations are by reference to the Inter-Society Color Council, National Bureau of Standards. Common color names are also used occasionally.

TREE

Size: Large.
Vigor: Vigorous.
Growth: Spreading and dense.
Form: Round topped.
Hardiness: Hardy.
Production: Very productive.
Bearing: Regular bearer.
Trunk:
- *Size.*—Medium.
- *Texture.*—Medium.
- *Bark color.*—Dark grayish yellowish brown [81. d.gy.yBr].
- *Lenticels.*—Numerous. Color: Moderate orange yellow [71. m.oY]. Average size: ⅛" to 5/16" [3.2–7.9 mm.].

Branches:
- *Size.*—Medium.
- *Texture.*—Medium.
- *Color.*—1st year wood topside: Light grayish red [18. 1.gy.R]. 1st year wood underside: Light yellow green [119. 1.YG]. Older wood: Moderate yellowish brown [77. m.yBr].
- *Lenticels.*—Numerous, small. Color: Dark orange yellow [72. d.OY]. Average size: 1 1/16" to ⅛" [1.6–3.2 mm.].

Leaves:
- *Size.*—Medium. Average length: 5½" [139.6 mm.]. Average width: ½" [38.1 mm.].

*Thickness.*—Medium.
*Form.*—Elliptical.
*Apex.*—Acuminate.
*Base.*—Acute.
*Surface.*—Smooth.
*Color.*—Dorsal surface: Moderate olive green [125. m.OLG]. Ventral surface: Moderate yellow green [120. m.YG].
*Margin.*—Finely serrate.
*Venation.*—Pinnately net veined.
*Petiole.*—Average length: 3/8" [9.5 mm.]. Average thickness: 1/16" [1.6 mm.]. Dorsal color: Brilliant yellow green [116. bril.YG]. Ventral color: Very Light yellowish green [134. v.l.yG].
*Stipules.*—Numerous. Average length: 3/16" [4.8 mm.].
*Glands.*—Numbers: 2 per leaf. Position: Alternately positioned on petiole and base of blade. Size: Very small. Form: Globose. Color: Brilliant yellow green [116. brill.YG].

Flower buds:
*Hardiness.*—Hardy.
*Size.*—Medium.
*Length.*—Medium.
*Form.*—Free.
*Surface.*—Pubescent.

Flowers:
*Blooming period.*—Medium as compared with other varieties.
*Size.*—Large.
*Color.*—Moderate pink [5. m.Pk].

FRUIT

Maturity when described: Hard ripe, Aug. 1, 1994.
Date of first picking: Jul. 29, 1994.
Date of last picking: Aug. 7, 1994.
Size: Uniform, large to medium.
*Average diameter axially.*—2 5/8" [66.7 mm.]
*Average transversely in suture plane.*—2 5/8" [66.7 mm.].
Form: Globose, uniform, symmetrical.
*Longitudinal section form.*—Circular to elliptical.
*Transverse section through diameter.*—Circular.
Suture: An inconspicuous line toward the base becoming a shallow groove toward the apex, extending from the base to beyond the apex, having a slight depression beyond the pistil point.
Ventral surface.—Rounded, lipped toward the apex on both sides.
Lips: Very equal.
Cavity: Flaring, elongated in suture plane, suture showing on one side.
*Depth.*—7/16" [11.1 mm.].
*Breadth.*—3/4" ]19.1 mm.].
Base: Somewhat cuneate and truncate.
Apex: Cuneate.
Pistil point: Negligible in length, mostly apical, depressed within the suture.
Stem: Medium.
*Average length.*—3/8" ]9.5 mm.].
*Average width.*—3/16" ]4.8 mm.].
Skin:
*Thickness.*—Medium.
*Texture.*—Medium.
*Tenacity.*—Tenacious to flesh.
*Tendency to crack.*—None observed.
*Color.*—Deep red [13. deep R] blending to a dark pink [6. d.Pk] over a pale yellow green [121. p.YG] background, with moderate orange yellow [71. m.OY] freckling toward the apex.

Flesh:
*Color.*—White [263. White] to pinkish white [9. pkwhite] with slight moderate red [15. m.R] streaking very close to the stone.
*Surface of pit cavity.*—Moderate red [15. m.R].
*Amygdalin.*—Wanting.
*Juice.*—Abundant, rich.
*Texture.*—Extremely firm, tough, non-melting.
*Fibers.*—Abundant. fine.
*Ripens.*—Evenly.
*Flavor.*—Non-acidic and sweet, averaging 18 brix.
*Aroma.*—Slight.
*Eating quality.*—Best.

STONE

Type: Clingstone.
Form: Very oval.
Base: Straight.
Apex: Acute.
Sides: Slightly unequal.
Surface: Horizontally furrowed toward the apex, pitted toward the base.
Ridges: Jagged toward the base.
Color: Moderate yellowish brown [77. m.YBr].
Pit wall: 1/4" [6.4 mm.] thick.
Tendency to split: Very slight.
Kernel:
*Form.*—Oval.
*Taste.*—Bitter.
*Viable.*—Yes.
*Average width.*—1/2" [12.7 mm.].
*Average length.*—3/4" [19.1 mm.].
*Skin color.*—Pale yellow [89. p.Y] when first cracked.
*Pellicle color.*—Dark brown [59. d.Br].
*Amygdalin.*—Abundant.

USE

Market: Fresh and long distance shipping.
Keeping quality: Very good.
Shipping quality: Very good.
Resistance to insects: No unusual susceptibilities noted.
Resistance to disease: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is most similar to its pollen grandparent, the Bradcrim (U.S. Plant Pat. No. 8,461), by producing white flesh nectarines that are non-acidic in flavor and virtually free from red texture bleeding, but is distinguished therefrom and an improvement thereon by producing fruit that ripens thirty days later, that is much firmer in texture, that is much sweeter in flavor, and that is clingstone instead of freestone.

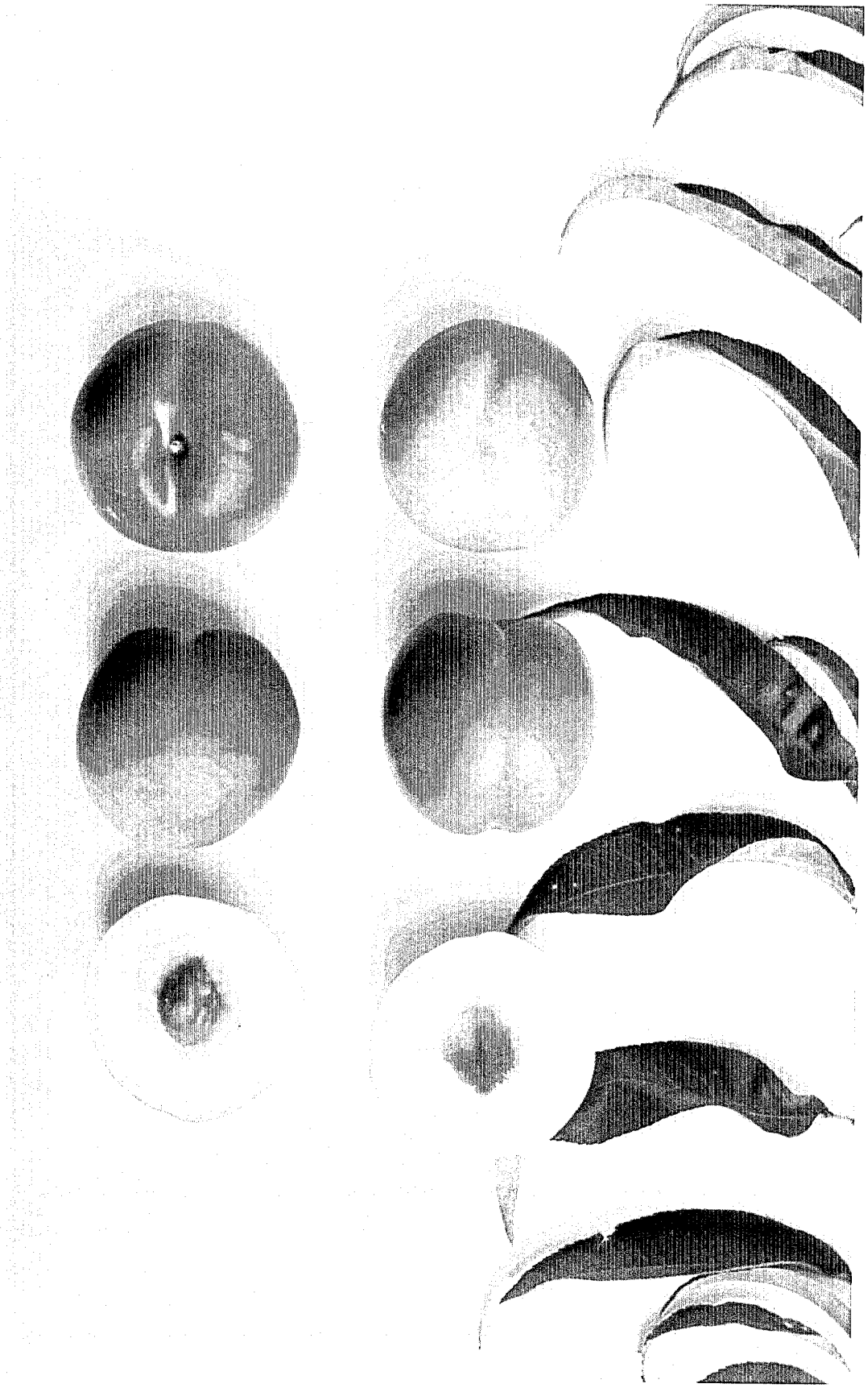

* * * * *